(12) United States Patent
Wierenga

(10) Patent No.: US 12,396,876 B1
(45) Date of Patent: *Aug. 26, 2025

(54) BLANKET SPLINT QUICK TIE SYSTEM AND METHOD FOR EMERGENCY MEDICAL CARE

(71) Applicant: Douglas Larry Wierenga, Saugatuck, MI (US)

(72) Inventor: Douglas Larry Wierenga, Saugatuck, MI (US)

( * ) Notice: Subject to any disclaimer, the term of this patent is extended or adjusted under 35 U.S.C. 154(b) by 0 days.

This patent is subject to a terminal disclaimer.

(21) Appl. No.: 19/192,560

(22) Filed: Apr. 29, 2025

Related U.S. Application Data

(63) Continuation of application No. 18/989,181, filed on Dec. 20, 2024, now Pat. No. 12,285,350.

(51) Int. Cl.
*A61F 5/058* (2006.01)

(52) U.S. Cl.
CPC .................................. *A61F 5/058* (2013.01)

(58) Field of Classification Search
CPC .... A61F 2002/4495; A61F 2013/00753; A61F 13/0283; A61F 2013/51139; A61F 2013/51449; A61F 2013/530664; A61F 5/058; A61F 5/05841; A61F 5/14
See application file for complete search history.

(56) References Cited

U.S. PATENT DOCUMENTS

| | | |
|---|---|---|
| 4,446,858 A | 5/1984 | Verter |
| 5,358,470 A | 10/1994 | Johnson |
| 5,651,143 A | 7/1997 | Zehrung |
| 5,897,519 A | 4/1999 | Shesol et al. |
| 6,406,449 B1 | 6/2002 | Moore et al. |
| 6,575,925 B1 | 6/2003 | Noble |
| 6,979,303 B2 | 12/2005 | Jestrabek-Hart |

(Continued)

FOREIGN PATENT DOCUMENTS

| | | | |
|---|---|---|---|
| CN | 110037846 | 7/2019 | |
| CN | 110037846 A | * 7/2019 | ............. A61F 5/058 |

(Continued)

*Primary Examiner* — Tarla R Patel
(74) *Attorney, Agent, or Firm* — King & Partners, PLC

(57) ABSTRACT

A medical splint securing system and method particularly suited for emergency medical care applications is disclosed. The system comprises three elongated fabric strips, each preferably measuring 5½ inches by 100 inches, permanently joined at their respective midpoints to form a unified structure with a central junction preferably measuring 5½ inches by 50 inches. This quick tie system simplifies and expedites the process of securing blanket roll splints in emergency situations, replacing traditional multiple-cravat methods. The unified design ensures adequate length for secure attachment while maintaining professional appearance during application. The system's versatility extends to use in sling and swathe immobilization techniques. The invention addresses key deficiencies in conventional splinting methods, including time consumption and inadequate securing length, while providing a more efficient and reliable solution for emergency medical responders. Methods of manufacture and application are also disclosed, emphasizing the system's practical implementation in emergency care scenarios.

9 Claims, 5 Drawing Sheets

(56) References Cited

U.S. PATENT DOCUMENTS

| | | | |
|---|---|---|---|
| 7,300,410 B1 | 11/2007 | Weber | |
| 9,895,254 B2 | 2/2018 | Bieber | |
| 11,206,894 B2 * | 12/2021 | Bushby | B26D 3/10 |
| 11,654,041 B2 | 5/2023 | Norfleet | |
| 12,064,368 B2 | 8/2024 | Gildersleeve et al. | |
| 12,285,350 B1 | 4/2025 | Wierenga | |
| 2004/0215119 A1 | 10/2004 | Avon | |
| 2012/0123311 A1 * | 5/2012 | Weidemann-Hendrickson | A61F 13/01021 602/53 |

FOREIGN PATENT DOCUMENTS

| | | | | |
|---|---|---|---|---|
| WO | WO 2019216776 | | 11/2019 | |
| WO | WO-2019216776 A1 | * | 11/2019 | A61F 5/0585 |

\* cited by examiner

BLANKET SPLINT QUICK TIE SYSTEM AND METHOD FOR EMERGENCY MEDICAL CARE

CROSS-REFERENCE TO RELATED APPLICATIONS

This application is a continuation of U.S. application Ser. No. 18/989,181, entitled "BLANKET SPLINT QUICK TIE SYSTEM AND METHOD FOR EMERGENCY MEDICAL CARE" filed Dec. 20, 2024, now U.S. Pat. No. 12,285,350—which is hereby incorporated herein by reference in its entirety, including all references cited therein.

COPYRIGHT NOTICE

This application includes material that is subject to copyright protection. The copyright owner has no objection to the facsimile reproduction by anyone of the patent disclosure, as it appears in the United States Patent and Trademark Office files or records, but otherwise reserves all copyright rights whatsoever.

STATEMENT REGARDING FEDERALLY SPONSORED RESEARCH OR DEVELOPMENT

Not applicable.

REFERENCE TO A SEQUENCE LISTING

Not applicable.

BACKGROUND OF THE INVENTION

1. Field of the Invention

The present invention generally relates to the field of emergency medical care equipment and procedures. More specifically, the invention pertains to an improved system and method for securing blanket roll splints in emergency medical situations, particularly in settings where rapid and reliable immobilization of injured body parts is crucial, such as in ski patrol emergency response scenarios.

2. Background of the Invention

In emergency medical care, particularly in environments such as ski resorts where rapid response to injuries is critical, medical professionals frequently employ blanket roll splints to immobilize injured limbs and joints. Traditionally, these splints have been secured using multiple triangular pieces of fabric known as cravats. While functional, this conventional approach presents several significant challenges in emergency situations where time and ease of application are of paramount importance.

The traditional method of securing blanket roll splints requires medical responders to manage multiple separate cravats, which can be cumbersome and time-consuming to position correctly. These difficulties are often exacerbated in adverse weather conditions or when treating patients in challenging terrain. Furthermore, the conventional cravats frequently prove inadequate in length, leading to situations where the splint becomes insufficiently secured to the patient during transport. This inadequacy not only compromises patient care but also requires additional time and attention from medical personnel to readjust and resecure the splint.

Additionally, the management of multiple separate pieces of fabric can present a less than professional appearance to patients and bystanders, potentially affecting their confidence in the care being provided. The current system's limitations become particularly apparent in high-stress emergency situations where every second counts and where medical responders need to maintain both efficiency and professionalism.

These and other objects of the present invention will become apparent in light of the present specification, claims, and drawings.

SUMMARY OF THE INVENTION

The following presents a simplified summary in order to provide a basic understanding of some aspects of the claimed subject matter. This summary is not an extensive overview, and is not intended to identify key/critical elements or to delineate the scope of the claimed subject matter. Its purpose is to present some concepts in a simplified form as a prelude to the more detailed description that is presented later.

The present invention provides an innovative solution to the challenges associated with securing blanket roll splints in emergency medical situations. At its core, the invention comprises a quick tie system featuring three strips of lightweight muslin fabric, each measuring approximately (+/− 10%) 5½ inches by approximately 100 inches, sewn together in the center to form a unified piece measuring approximately 5½ inches by approximately 50 inches at the connection point.

This novel design significantly streamlines the process of securing blanket roll splints while simultaneously improving the reliability and professional appearance of the final application. The invention represents a substantial improvement over traditional methods by eliminating the need for multiple separate cravats and providing consistent, adequate length for secure attachment.

BRIEF DESCRIPTION OF THE DRAWINGS

Certain embodiments of the present invention are illustrated by the accompanying figures. It will be understood that the figures are not necessarily to scale and that details not necessary for an understanding of the invention or that render other details difficult to perceive may be omitted.

It will be further understood that the invention is not necessarily limited to the particular embodiments illustrated herein.

Figure 1:
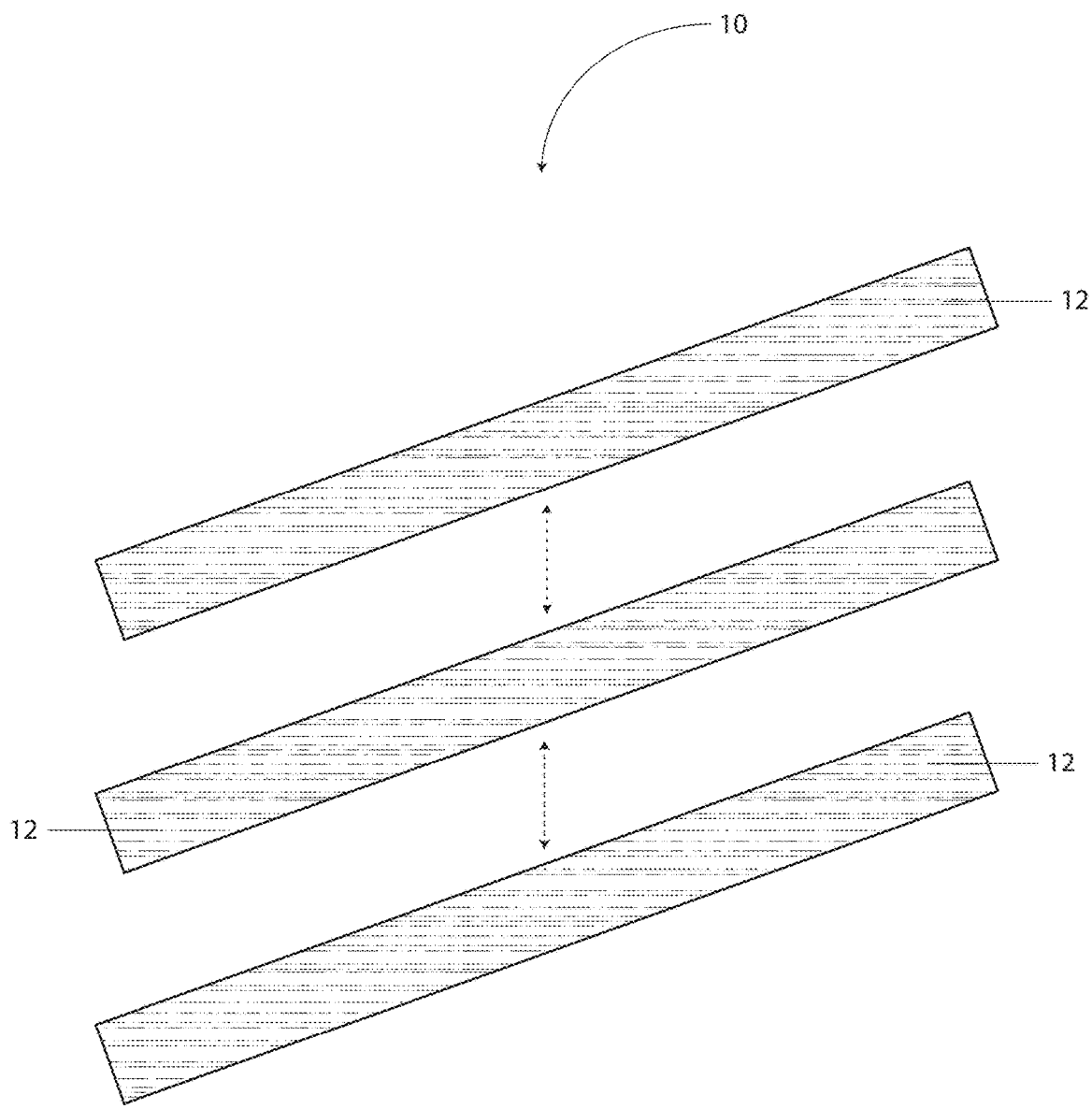

The invention will now be described with reference to the drawings wherein:

FIG. 1 is an exploded perspective view of the quick tie system of the present invention.

Figure 2:
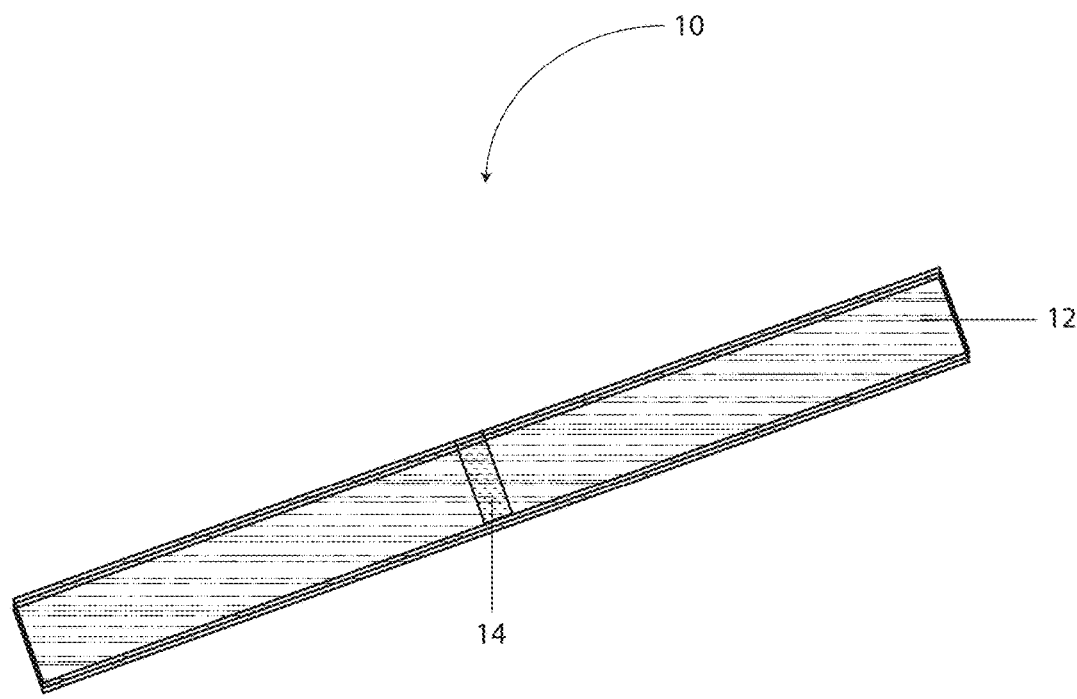

FIG. 2 is an assembled perspective view of the quick tie system of the present invention.

Figure 3:
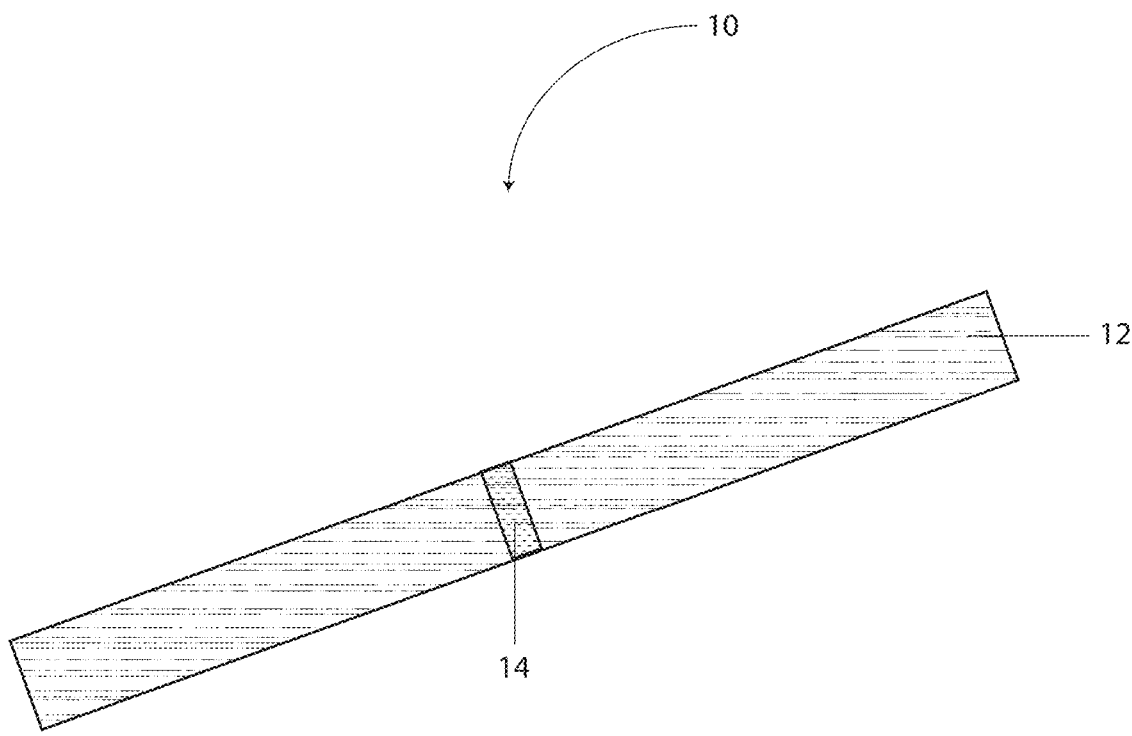

FIG. 3 is a top view of the quick tie system of FIG. 2. The bottom view is generally a mirror image of the top view.

Figure 4:
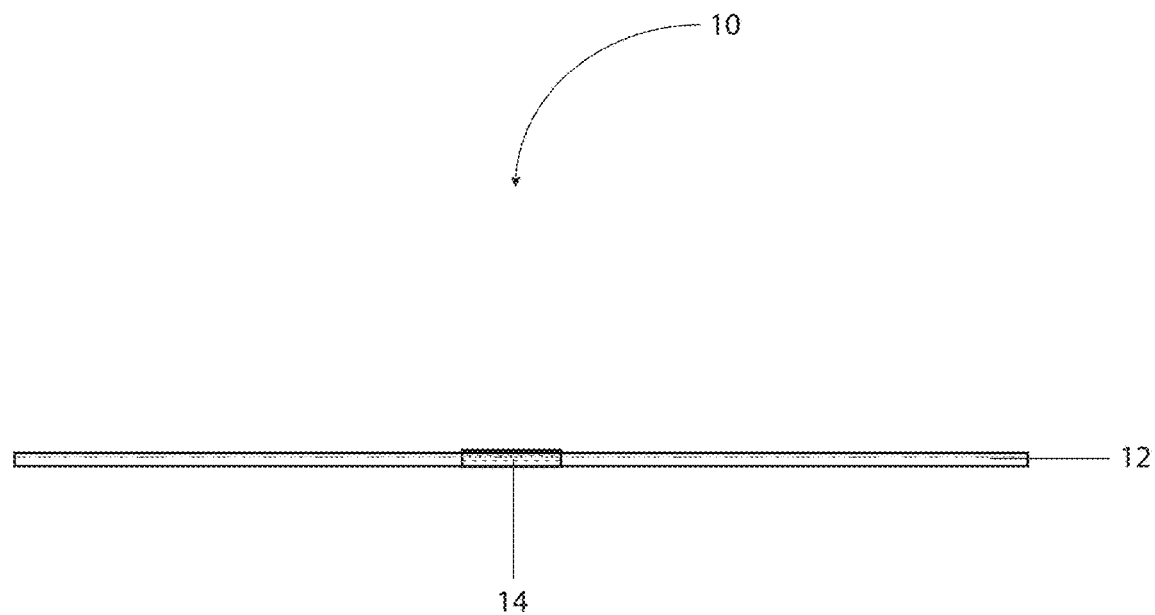

FIG. 4 is a side view of the quick tie system of FIG. 2.

Figure 5:
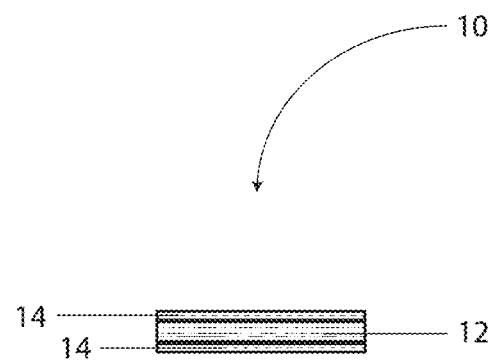

FIG. 5 is an end view of the quick tie system of FIG. 2.

DETAILED DESCRIPTION OF THE INVENTION

While this invention is susceptible of embodiment in many different forms and applications, there are shown in the drawings and described herein in detail several specific embodiments with the understanding that the present disclosure is to be considered as an exemplification of the principles of the invention and is not intended to limit the invention to the embodiments illustrated.

It will be understood that like or analogous elements and/or components, referred to herein, may be identified throughout the drawings by like reference characters. In addition, it will be understood that the drawings are merely schematic representations of one or more embodiments of the invention, and some of the components may have been distorted from their actual scale for purposes of pictorial clarity.

The following detailed description presents various embodiments of the invention with reference to the accompanying figures. As is shown in FIGS. 1-5, quick tie system 10 includes generally rectangular swatches/strips 12, and securement swatch 14.

The present invention, in its preferred embodiment, comprises an integrated quick tie system specifically engineered for securing blanket roll splints in emergency medical scenarios. The following detailed description, when taken in conjunction with the accompanying drawings, will provide a complete understanding of the invention's structure, function, and advantages.

Structure and Materials

The quick tie system consists of three elongated strips of lightweight muslin fabric, each preferably precisely dimensioned at 5½ inches in width and 100 inches in length. These strips are permanently joined together at their respective midpoints through a secure stitching process, creating a central junction point measuring 5½ inches by 50 inches. The choice of lightweight muslin fabric is particularly significant, as this material provides an optimal balance of strength, flexibility, and durability while maintaining minimal bulk when stored in emergency medical kits. While muslin represents the preferred embodiment, the invention contemplates the use of various alternative natural and synthetic materials, each offering distinct advantages in specific deployment scenarios. Natural fiber alternatives may include lightweight cotton broadcloth, cotton gauze, cotton twill, linen, cambric, lightweight canvas, cotton poplin, cotton lawn fabric, bamboo fabric, hemp textile, ramie fiber fabric, or lightweight wool gabardine. These natural alternatives maintain the essential breathability characteristics while offering varying degrees of strength and texture. Synthetic and synthetic-blend alternatives may include lightweight polyester fabric, nylon ripstop, polyester-cotton blend (polycotton), spandex-cotton blend offering minor elasticity for enhanced conformity to irregular shapes, rayon, modal, lyocell, microfiber polyester, nylon-cotton blend, polyester-spandex blend providing controlled stretch characteristics, or aramid fiber fabric for enhanced durability. Several of these alternatives, particularly the synthetic blends incorporating spandex or elastane, can provide a minor degree of elasticity (typically 2-5% stretch) which may prove advantageous in certain medical scenarios where gentle compression or conformity to irregular body contours is desired. The selection of any alternative material should maintain the critical characteristics of being lightweight, durable, and capable of maintaining structural integrity under emergency medical use conditions while being suitable for standard sterilization procedures.

In further embodiments, the fabric material may be treated with or incorporate various antimicrobial compounds and substances to enhance infection prevention capabilities when in contact with a patient. Such antimicrobial properties may be achieved through several methods, including but not limited to: incorporation of silver nanoparticles during fiber production, application of quaternary ammonium compounds, treatment with copper-based antimicrobial agents, integration of zinc oxide particles, application of chitosan-based compounds, treatment with triclosan, incorporation of PHMB (polyhexamethylene biguanide), or impregnation with iodine-based antimicrobial substances. The antimicrobial properties may be achieved through either topical application of these compounds to the finished fabric, integration during the fiber manufacturing process, or through chemical bonding to the fiber structure itself. These treatments may be applied to any of the aforementioned fabric materials, with specific antimicrobial compounds selected based on compatibility with the base material and intended clinical application. The antimicrobial properties are designed to maintain efficacy through multiple uses and standard medical cleaning procedures, providing an additional layer of protection in emergency medical scenarios where environmental conditions may increase infection risks. Furthermore, the antimicrobial treatments are formulated to remain stable and effective without causing skin irritation or adverse reactions when in direct contact with the patient's skin during extended periods of splint application.

In alternative embodiments, the terminal ends of each fabric strip may incorporate hook-and-loop fastening systems to facilitate rapid and secure closure without the need for traditional knot-tying. Such fastening systems may comprise complementary hook and loop portions affixed to opposing sides of each strip end, extending approximately 8 to 12 inches from each terminal end, thereby providing substantial adjustability and secure engagement surfaces. The hook-and-loop fasteners may be permanently attached through various means including, but not limited to, sewn attachment, heat bonding, or adhesive lamination, with the attachment method selected to ensure durability through repeated use and standard medical cleaning procedures. This fastening system allows for rapid application and adjustment of the splint securing system, particularly advantageous in emergency situations where time is critical or when wearing medical gloves that might otherwise complicate traditional knot-tying. The hook-and-loop system may be designed with a graduated or variable engagement surface to allow for precise tension control, and may incorporate visual indicators or alignment marks to facilitate proper engagement. Furthermore, the hook-and-loop fastening system can be engineered to maintain secure closure even under dynamic movement conditions typically encountered during patient transport, while simultaneously allowing for rapid removal or adjustment when necessary for patient assessment or treatment modification.

The stitching pattern at the central junction point is specifically designed to maintain the structural integrity of the connection while allowing each strip to move and conform as needed during application. This unified construction eliminates the need for managing multiple separate pieces while ensuring that adequate length is always available for proper securing of the splint.

Method of Use

The application method of the quick tie system represents a significant advancement over traditional techniques. In one embodiment, when implementing the system, the medical responder first positions the central junction point at the desired location on the blanket roll splint. The three extending strips can then be wrapped around the splint and patient's limb in a systematic manner, with each strip providing optimal coverage and security. In another embodiment, when implementing the system, the medical responder first positions the central junction point at one end of a blanket that has been folded into a long narrow shape. The blanket is then rolled up starting at the end where the splint has been applied. This integrates the quick tie with the blanket and completes the field assembly of the blanket roll split. The split consists of a rolled blanket with three equal strips extending from each end of blanket. The blanket roll splint is then secured to the patient. The goal of the medical responder is to stabilize the injury in a position of comfort for transport. Since the three strips of fabric are secured at their center the medical responder no longer has to take time to make sure that they are using the ends of the same cravat when securing the splint. Having ties of adequate and equal length speeds up the process of applying the splint.

Applying a Blanket Roll Splint to a Shoulder with Quick Tie System

To apply a blanket roll splint to an injured shoulder in an emergency situation, begin by selecting an appropriate blanket that will provide both support and temperature control for the patient. First, take the blanket and carefully roll or fold it to achieve the right size and thickness needed for the particular patient's body structure. Once prepared, position the rolled blanket strategically under the patient's affected arm, placing it securely in their armpit area. The next crucial step involves maintaining firm pressure while wrapping the blanket around the injured shoulder area, ensuring it provides adequate support without being overly tight. As you continue the process, guide the remaining portion of the blanket roll across the patient's body, using it to create a secure cradle for the forearm and hand. Finally, assess the stability of your splint and perform a CMS (circulation, motion, sensation) check to ensure the splint isn't impeding blood flow or nerve function.

The 100-inch length of each strip ensures sufficient material for proper securing, even when dealing with larger limbs or multiple wrapping requirements. This adequate length provision directly addresses one of the primary deficiencies of traditional cravat systems, where insufficient length often leads to compromised security and potential splint failure during patient transport.

Advantages in Emergency Settings

The quick tie system provides several distinct advantages in emergency medical situations: (1) Time Efficiency—The unified construction eliminates the need to locate and manage multiple separate pieces, significantly reducing the time required for splint application; (2) Reliability—The consistent length and integrated design ensure that adequate material is always available for proper securing, reducing the risk of splint loosening during patient transport; (3) Professional Appearance—The systematic nature of the design results in a more organized and professional-looking application, which can enhance patient confidence and comfort; and (4) Versatility—While primarily designed for blanket roll splints, the system can be effectively utilized for sling and swathe immobilization techniques, expanding its utility in emergency medical scenarios.

The foregoing description merely explains and illustrates the invention and the invention is not limited thereto except insofar as the appended claims are so limited, as those skilled in the art who have the disclosure before them will be able to make modifications without departing from the scope of the invention.

While certain embodiments have been illustrated and described, it should be understood that changes and modifications can be made therein in accordance with ordinary skill in the art without departing from the technology in its broader aspects as defined in the following claims.

The embodiments, illustratively described herein may suitably be practiced in the absence of any element or elements, limitation or limitations, not specifically disclosed herein. Thus, for example, the terms "comprising," "including," "containing," etcetera shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the claimed technology. Additionally, the phrase "consisting essentially of" will be understood to include those elements specifically recited and those additional elements that do not materially affect the basic and novel characteristics of the claimed technology. The phrase "consisting of" excludes any element not specified.

The present disclosure is not to be limited in terms of the particular embodiments described in this application. Many modifications and variations can be made without departing from its spirit and scope, as will be apparent to those skilled in the art. Functionally equivalent methods and compositions within the scope of the disclosure, in addition to those enumerated herein, will be apparent to those skilled in the art from the foregoing descriptions. Such modifications and variations are intended to fall within the scope of the appended claims. The present disclosure is to be limited only by the terms of the appended claims, along with the full scope of equivalents to which such claims are entitled. It is to be understood that this disclosure is not limited to particular systems and/or methods. It is also to be understood that the terminology used herein is for the purpose of describing particular embodiments only, and is not intended to be limiting.

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, particularly in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etcetera. As a non-limiting example, each range discussed herein can be readily broken down into a lower third, middle third and upper third, etcetera. As will also be understood by one skilled in the art all language such as "up to," "at least," "greater than," "less than," and the like, include the number recited and refer to ranges which can be subsequently broken down into subranges as discussed above. Finally, as will be understood by one skilled in the art, a range includes each individual member.

All publications, patent applications, issued patents, and other documents referred to in this specification are herein incorporated by reference as if each individual publication, patent application, issued patent, or other document was specifically and individually indicated to be incorporated by reference in its entirety. Definitions that are contained in text incorporated by reference are excluded to the extent that they contradict definitions in this disclosure.

Other embodiments are set forth in the following claims.

What is claimed and desired to be secured by Letters Patent of the United States is:

1. A medical splint securing system, comprising:
   three elongated fabric strips, each strip having:
      a width of approximately 5½ inches;
      a length of approximately 100 inches;
   wherein said strips are permanently joined at their respective midpoints to form a unified structure;
   wherein said joined midpoints form a central junction measuring approximately 5½ inches by 50 inches; and
   wherein said system is configured to secure a blanket roll splint to a patient's body part.

2. The system of claim 1, wherein said fabric strips comprise lightweight muslin material.

3. The system of claim 1, wherein said permanent joining is accomplished through stitching.

4. The system of claim 1, wherein said fabric strips are configured to maintain consistent tension during patient transport.

5. The system of claim 1, further comprising color-coding on at least one strip to indicate proper alignment during application.

6. The system of claim 1, wherein the unified structure is configured to be stored in a compact configuration within an emergency medical supply bag.

7. The system of claim 1, wherein each strip is configured to maintain structural integrity under emergency medical use conditions.

8. The system of claim 1, wherein the unified structure is configured for alternative medical uses including sling and swathe immobilization.

9. A medical splint securing system, consisting of:
   three elongated fabric strips, each strip having:
      a width of 5½ inches;
      a length of 100 inches;
   wherein said strips are permanently joined at their respective midpoints to form a unified structure;
   wherein said joined midpoints form a central junction measuring 5½ inches by 50 inches;
   wherein said system is configured to secure a blanket roll splint to a patient's body part;
   wherein said fabric strips are fabricated from muslin material;
   wherein said permanent joining is accomplished through stitching; and
   wherein said fabric strips are configured to maintain consistent tension during patient transport.

* * * * *